(12) United States Patent
Chou et al.

(10) Patent No.: US 8,523,357 B2
(45) Date of Patent: Sep. 3, 2013

(54) FUNDUS OPTICAL IMAGE DEVICE

(75) Inventors: Chung-Cheng Chou, Luzhu Township (TW); William Wang, Taoyuan (TW)

(73) Assignee: Crystalvue Medical Corporation, Guishan Township, Taoyuan County (TW)

(*) Notice: Subject to any disclaimer, the term of this patent is extended or adjusted under 35 U.S.C. 154(b) by 0 days.

(21) Appl. No.: 13/189,173

(22) Filed: Jul. 22, 2011

(65) Prior Publication Data

US 2012/0026465 A1 Feb. 2, 2012

(30) Foreign Application Priority Data

Jul. 28, 2010 (TW) .............................. 99124981 A

(51) Int. Cl.
*A61B 3/14* (2006.01)
*A61B 3/135* (2006.01)

(52) U.S. Cl.
CPC .. *A61B 3/14* (2013.01); *A61B 3/135* (2013.01)
USPC ......................................... 351/206; 351/214

(58) Field of Classification Search
CPC .................................. A61B 3/14; A61B 3/135
USPC .................................. 351/205, 206, 210, 214
See application file for complete search history.

(56) References Cited

U.S. PATENT DOCUMENTS

| 6,079,828 A * | 6/2000 | Fujieda ........................ 351/206 |
| 7,798,642 B2 * | 9/2010 | Itoh et al. ..................... 351/206 |
| 2003/0025876 A1 * | 2/2003 | Nanjo ........................... 351/206 |

FOREIGN PATENT DOCUMENTS

| TW | 200630068 A | 9/2006 |
| TW | I292048 B | 1/2008 |

* cited by examiner

*Primary Examiner* — Huy K Mai
(74) *Attorney, Agent, or Firm* — Cheng-Ju Chiang

(57) ABSTRACT

A fundus optical image device includes a light source, a first optical element set and a second optical element set. The first optical element set includes a first diaphragm. The light emitted from the light source passes through the first diaphragm and reaches a fundus through the first optical element set. The second optical element set includes a second diaphragm. The light is reflected by the fundus and then passes through the second diaphragm to present an image of the fundus. At least one of the first diaphragm and the second diaphragm is a microarray diaphragm.

10 Claims, 5 Drawing Sheets

FUNDUS OPTICAL IMAGE DEVICE

CROSS REFERENCE TO RELATED APPLICATIONS

This Non-provisional application claims priority under 35 U.S.C. §119(a) on Patent Application No(s). 099124981 filed in Taiwan, Republic of China on Jul. 28, 2010, the entire contents of which are hereby incorporated by reference.

BACKGROUND OF THE INVENTION

1. Field of Invention

The present invention relates to an optical inspection device and, in particular, to an optical image inspection device for eyes.

2. Related Art

The common eye inspection device includes the pneumatic tonometer, kerato-refractometer, fundus optical image device, and the likes. In particular, the fundus optical image device is an optical inspection device for observing the fundus.

The fundus optical image device is mainly used to inspect the pathological changes of the macula lutea and the optic nerve of the retina. It can be directly applied to inspect the fundus without administering the mydriatic eye drops to the eyes. Thus, the fundus optical image device can provide the simple, fast, precise and cheap inspection. Moreover, through the fundus optical image device, some fundus pathological changes, such as glaucoma, neuropapillitis, or macular degeneration, can be inspected out.

In addition, since the fundus inspection can directly observe the blood vessels, the fundus optical image device can further inspect some other symptoms such as diabetes retinopathy.

As shown in FIG. 1, a conventional fundus optical image device 1 mainly includes a light unit 11, a light-path unit 12, an image capturing unit 13 and an observation unit 14. The light unit 11 includes an optical lens set for directing a light emitted by a light source to the fundus 21 of an eye 2. Then, the light reflected by the fundus 21 enters the light-path unit 12 for presenting the image of the fundus 21, and the image capturing unit 13 captures the image. After that, the user can observe the image of the fundus 21 and/or adjust the resolution thereof by the observation unit 14.

As mentioned above, in the conventional fundus optical image device 1, the diaphragm of the light-path unit 12 is designed as the fix type, so that the aperture size or aperture shape of the diaphragm is fixed and can not be changed. In brief, the conventional diaphragm can not provide adaptive changes for different light sources or different patients (e.g. with different eyeball curvatures and pupil sizes).

Therefore, it is an important subject of the invention to provide a fundus optical image device with changeable diaphragm dimension.

SUMMARY OF THE INVENTION

To achieve the foregoing subject, an objective of the present invention is to provide a fundus optical image device with changeable diaphragm dimension.

To achieve the above objective, the present invention discloses a fundus optical image device including a light source, a first optical element set and a second optical element set. The first optical element set includes a first diaphragm. The light emitted from the light source passes through the first diaphragm and reaches a fundus through the first optical element set. The second optical element set includes a second diaphragm. The light is reflected by the fundus and then passes through the second diaphragm to present an image of the fundus. At least one of the first diaphragm and the second diaphragm is a microarray diaphragm.

In one embodiment, the microarray diaphragm is an electrochromic microarray diaphragm, a liquid crystal microarray diaphragm, an electrowetting microarray diaphragm, or a dielectrophoresis microarray diaphragm.

In one embodiment, the first diaphragm has an annular light penetrable area, and the second diaphragm has a center light penetrable area.

In one embodiment, the first optical element set includes at least a lens and a spectroscope. The light emitted from the light source passes through the lens, the first diaphragm and the spectroscope in order, and then reaches the fundus.

In one embodiment, the second optical element set further includes at least a lens. The second diaphragm is disposed between the lens and the fundus, and the lens may be a curvature-adjustable lens.

In one embodiment, the first diaphragm and the second diaphragm are both microarray diaphragms.

In one embodiment, the fundus optical image device further includes an observation module for observing the image of the fundus through the second optical element set.

In one embodiment, the fundus optical image device further includes an image capturing module for capturing the image of the fundus through the second optical element set.

As mentioned above, the diaphragm of the fundus optical image device of the invention is a microarray diaphragm, so that the aperture size or aperture shape of the diaphragm is changeable. Thus, the diaphragm of the invention can provide adaptive changes for different light sources and/or different patients (e.g. with different eyeball curvatures and pupil sizes).

BRIEF DESCRIPTION OF THE DRAWINGS

The invention will become more fully understood from the detailed description and accompanying drawings, which are given for illustration only, and thus are not limitative of the present invention, and wherein.

DETAILED DESCRIPTION OF THE INVENTION

The present invention will be apparent from the following detailed description, which proceeds with reference to the accompanying drawings, wherein the same references relate to the same elements.

Figure 1:
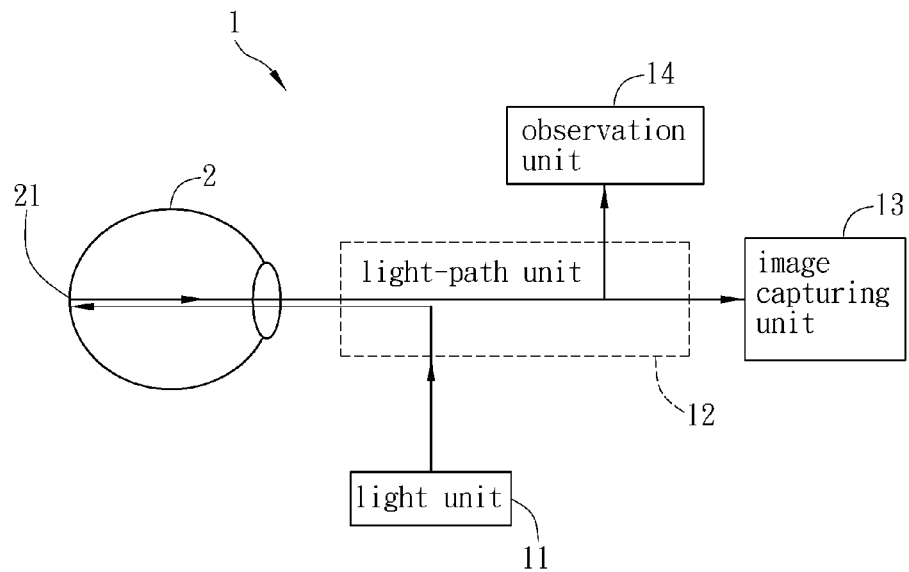
FIG. 1 is a schematic diagram showing a conventional fundus optical image device.
Figure 2:
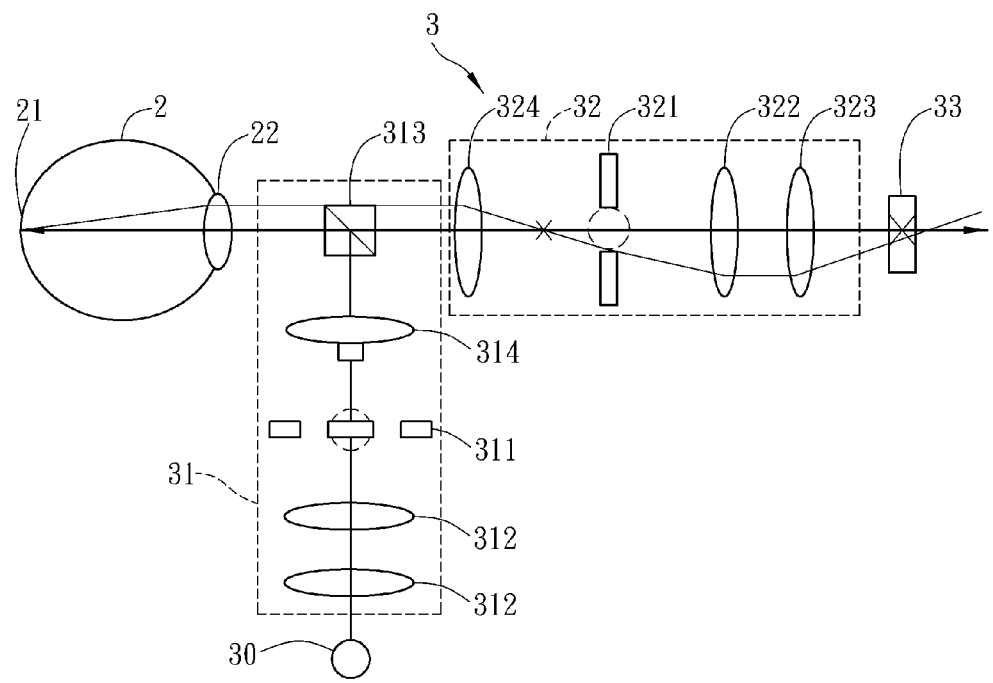
FIG. 2 is a schematic diagram showing a fundus optical image device according to a preferred embodiment of the invention.

With reference to FIG. 2, a fundus optical image device 3 for inspecting a fundus 21 includes a light source 30, a first optical element set 31 and a second optical element set 32. The first optical element set 31 includes a first diaphragm 311. The light emitted from the light source 30 passes through the first diaphragm 311 and reaches a fundus 21 of an eye 2 through the first optical element set 31. The second optical element set 32 includes a second diaphragm 321. The light is reflected by the fundus 21 and then passes through the second diaphragm 321 to present an image of the fundus 21.

In this embodiment, the first optical element set 31 further includes at least one lens 311, a spectroscope 313, and a lens 314. The second optical element set 32 further includes two lenses 322 and 323. The second diaphragm 321 is disposed between the lens 322 and the fundus 21, and the lens 323 cooperates with the lens 322 for adapting to the pupils 22 of different eyes 2.

At least one of the first diaphragm 311 and the second diaphragm 321 is a microarray diaphragm. The microarray diaphragm is, for example, an electrochromic microarray diaphragm, a liquid crystal microarray diaphragm, an electrowetting microarray diaphragm, or a dielectrophoresis microarray diaphragm.

Otherwise, the first diaphragm 311 and the second diaphragm 321 can be both microarray diaphragms.

The first diaphragm 311 has an annular light penetrable area, and the second diaphragm 321 has a center light penetrable area. Thus, the light path traveling to the fundus 21 and the light path reflected from the fundus 21 are not overlapped.

The light emitted from the light source 30 passes through the lens 312, the first diaphragm 311, the spectroscope 313, and the pupil 22 of the eye 2 in order, and then reaches the fundus 21 of the eye 2. In addition, the light reflected by the fundus 21 passes through the pupil 22, the spectroscope 313, the lens 324, the second diaphragm 321, the lens 322 and the lens 323 in order, thereby presenting the image of the fundus 21.

Besides, the fundus optical image device 3 further includes an image capturing module 33 for capturing the image of the fundus 21 through the second optical element set 32.

Moreover, the fundus optical image device 3 may further include an observation module for observing the image of the fundus 21 through the second optical element set 32. The observation module can be disposed at the location of the image capturing module 33.

The lens 322 can be moved forward and backward to alter the light path, thereby allowing the fundus optical image device 3 to adapt to the pupils 22 of different eyes 2. In addition, the lens 322 can be a curvature-adjustable lens, which can alter the focus of the lens according to the optical property itself, thereby allowing the fundus optical image device 3 to adapt to the pupils 22 of different eyes 2. When utilizing the curvature-adjustable lens, it is unnecessary to preserve the space for moving the lens, so that the dimension of the fundus optical image device 3 can be minimized.

Figure 3A:
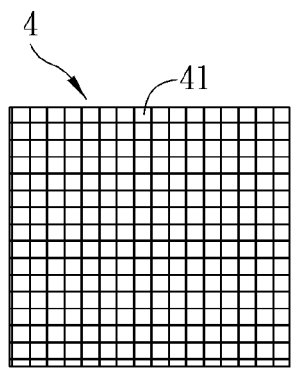
FIGS. 3A to 3C are schematic diagrams showing the microarray diaphragm.
Figure 3B:
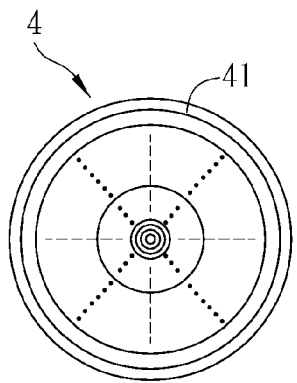
Figure 3C:
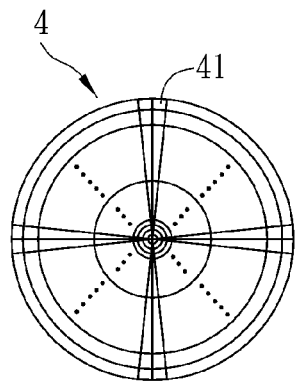

Reference to FIGS. 3A to 3C, the microarray diaphragm 4 includes a plurality of switch units, which are arranged in a two-dimensional array as shown in FIG. 3A, in an annular shape as shown in FIG. 3B, or in an arc shape as shown in FIG. 3C. The microarray diaphragm 4 can substitute for the first 311 or the second diaphragm 321.

In the microarray diaphragm 4, the switch units 41 are respectively controlled by, for example, the voltage signals. The Switch units 41 can be made by electrochromic materials. The electrochromic is the procedure of applying a voltage differential to the material so that the material can be transformed from the original transparent state to the colorful state. The electrochromic material is usually colorless while not applying any voltage to it, and is colorful while applying voltage to it. For example, when a positive voltage is applied to the electrochromic material, it can be transformed from the original colorless to the color of deep blue. If the voltage is reversed, the electrochromic material can be transformed from the color of deep blue back to the colorless. This embodiment is to applying different voltages to the switch units 41 for changing the transmittance, so that the microarray diaphragm 4 can have a changeable light penetrable area.

Alternatively, the microarray diaphragm 4 may also be made of liquid crystal materials. By using voltages to control the rotation of the liquid crystal, switch units 41 can present different transmittances. Thus, the microarray diaphragm 4 can have a changeable light penetrable area.

Besides, the switch units 41 of the microarray diaphragm 4 may be made of the electrowetting material or dielectrophoresis material. The electrowetting material utilizes the liquid for altering its focus, so that it has the advantages of high performance, low cost, compact, and low power consumption. This technique mainly uses the property of the electro-conductive aqueous liquid and the nonconductive oil. When using these two kinds of liquids to construct the lens structure, the contact area between the aqueous liquid and the oil can be altered by applying different currents. Accordingly, the expansion of the contact area allows the increase of the curvature, so that the focus can be moved similar to the focusing operation. The switch unit 41 can alter its focus to control whether to permit the light passing through it to enter the next component.

Alternatively, the switch unit 41 may be made of the dielectrophoresis material. In the dielectrophoresis material, the electrical couples induced by the external electric field and the interaction of the external electric field can drive the particles. Thus, the particles do not need to carry electricity, and they can be driven by the dielectrophoresis force by applying alternating voltage.

Figure 4A:
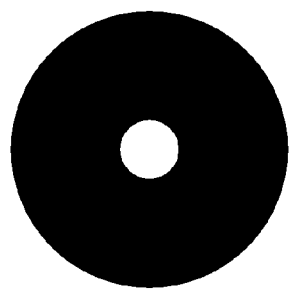
FIGS. 4A and 4B are schematic diagrams of the diaphragm of FIG. 2.

If the first diaphragm 311 is made of the microarray diaphragm 4, the switch units 41 are controlled by the voltage signals so as to present the annular light penetrable area and the center light non-penetrable area as shown in FIG. 4A.

Figure 4B:
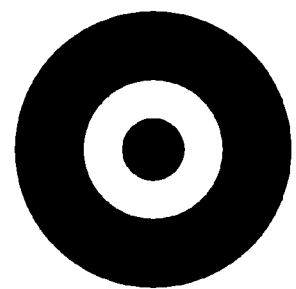

In addition, if the second diaphragm 321 is made of the microarray diaphragm 4, the switch units 41 are controlled by the voltage signals so as to present the center light penetrable area as shown in FIG. 4B.

Figure 5:
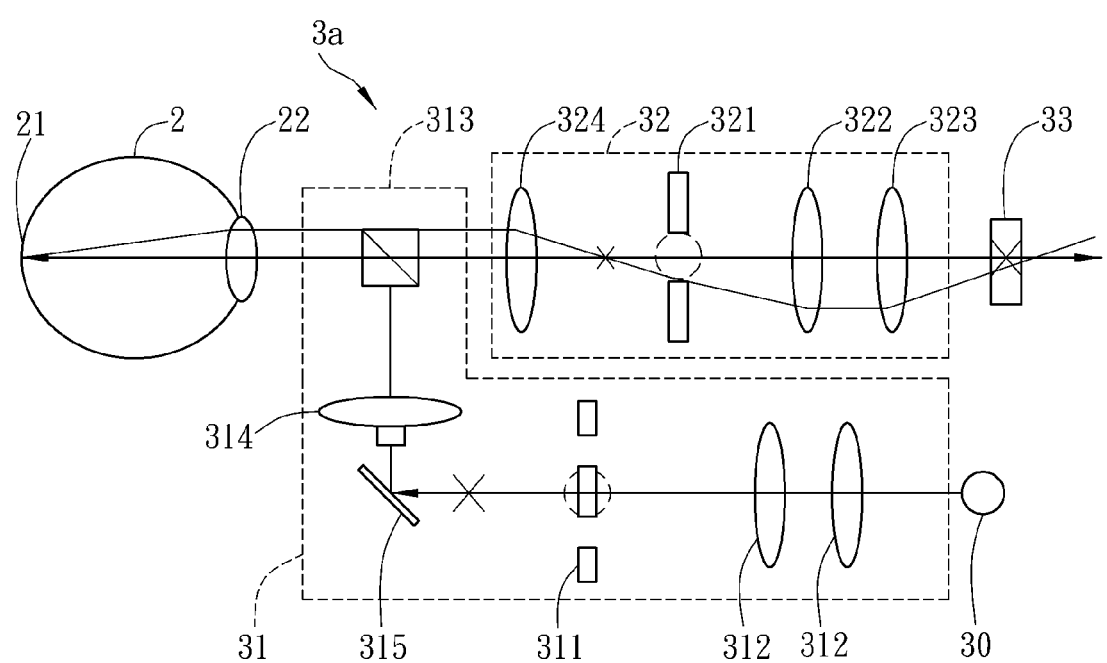
FIG. 5 is a schematic diagram showing a fundus optical image device according to another preferred embodiment of the invention.

Referring to FIG. 5, a fundus optical image device 3a of another embodiment is different from the previous embodiment in that the first optical element set 31 further includes a reflective mirror 315. The light emitted from the light source 30 passes through the lens 312, the first diaphragm 311, the reflective mirror 315, the lens 314, the spectroscope 313 and the pupil 22 of the eye 2 in order, and then reaches the fundus 21 of the eye 2. In addition, the light reflected by the fundus 21 passes through the pupil 22, the spectroscope 313, the lens 324, the second diaphragm 321, the lens 322 and the lens 323 in order, thereby presenting the image of the fundus 21.

Figure 6:
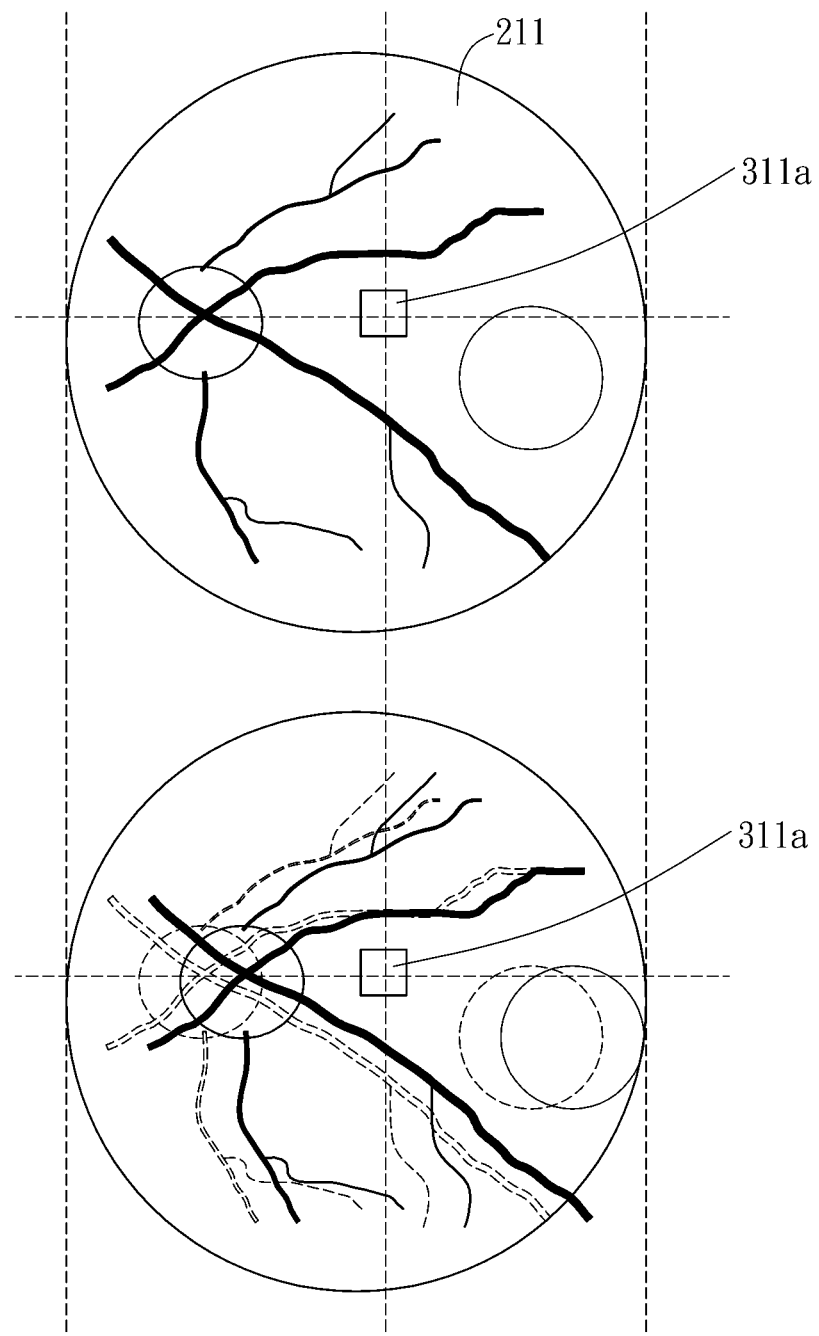
FIG. 6 is a schematic diagram of the microarray diaphragm, wherein an experimental target pattern is observed.

As shown in FIG. 6, when the image capturing module 33 captures the image 211 of the fundus 21, the first diaphragm 311 made of the microarray diaphragm can be controlled to present the target pattern 311a. In other words, the target pattern 311a and the image 211 of the fundus 21 can be captured by the image capturing module 33, or be presented on the observation module. Accordingly, the user can easily observe the motion of the eyeball through the image capturing module 33 or the observation module. In addition, the second diaphragm 321 made of the microarray diaphragm can provide the same or similar effect.

Figure 7:
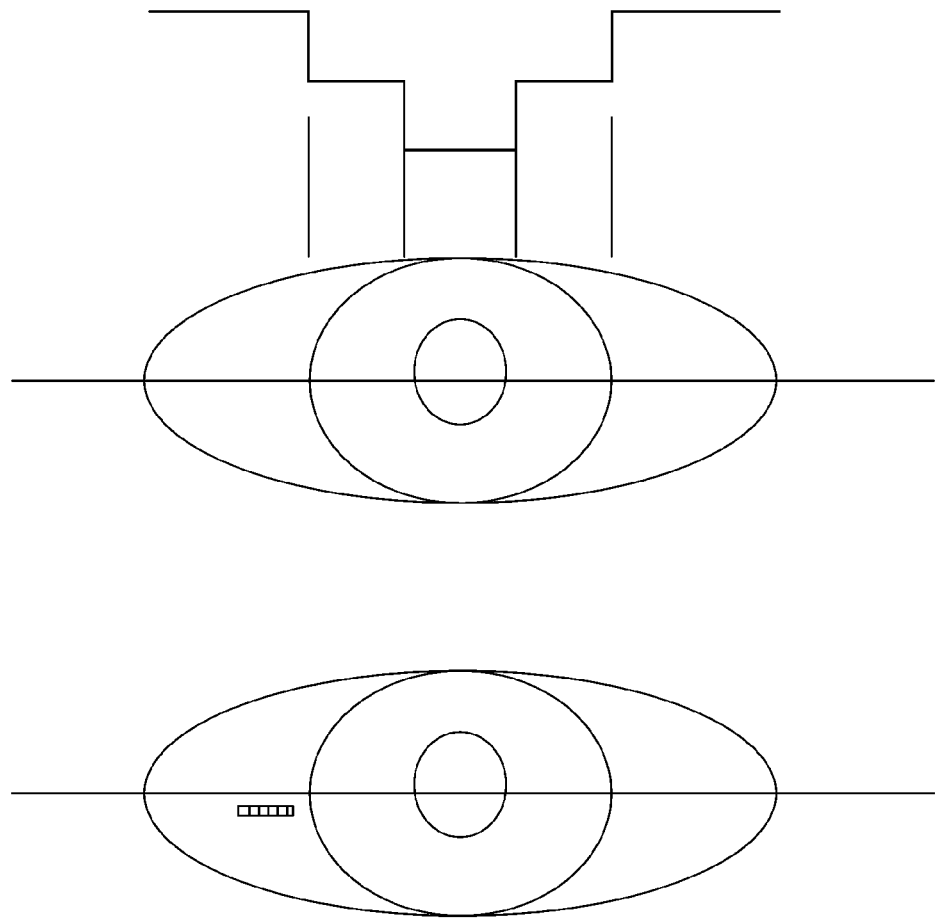
FIG. 7 is a schematic diagram of the microarray diaphragm, which is used as a mask.

As shown in FIG. 7, the first diaphragm 311 made of the microarray diaphragm can be used as a mask, and the transmittance of the mask can have stepwise variations. Accordingly, the pattern changes thereof can provide the reference for tracking the motion of the eyeball. For example, the microarray diaphragm 31 may present the pattern of the eye, so that the motion of the eyeball can be observed by realizing the light reflection variations of the fundus (see the point indicated by the arrow in FIG. 7). In addition, the second diaphragm 321 made of the microarray diaphragm can provide the same or similar effect.

As mentioned above, the diaphragm of the fundus optical image device of the invention is a microarray diaphragm, so that the aperture size or aperture shape of the diaphragm is changeable. Thus, the diaphragm of the invention can provide adaptive changes for different light sources and/or different patients (e.g. with different eyeball curvatures and pupil sizes).

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A fundus optical image device, comprising:
   a light source emitting a light;
   a first optical element set comprising a first diaphragm and a spectroscope, wherein the light emitted from the light source passes through the first diaphragm and the spectroscope and then reaches a fundus through the first optical element set; and
   a second optical element set comprising a second diaphragm and a first lens, wherein the light is reflected by the fundus and then passes through the spectroscope, the first lens and the second diaphragm in order, thereby presenting an image of the fundus;
   wherein, at least one of the first diaphragm and the second diaphragm is a microarray diaphragm, the first lens is disposed between the spectroscope and the second diaphragm;
   wherein the microarray diaphragm has a plurality of switch units, and each of the plurality of switch units is controlled by a voltage to change its color and transmittance.

2. The fundus optical image device according to claim 1, wherein the microarray diaphragm is an electrochromic microarray diaphragm, a liquid crystal microarray diaphragm, an electrowetting microarray diaphragm, or a dielectrophoresis microarray diaphragm.

3. The fundus optical image device according to claim 1, wherein the first diaphragm has an annular light penetrable area.

4. The fundus optical image device according to claim 1, wherein the second diaphragm has a center light penetrable area.

5. The fundus optical image device according to claim 1, wherein the first optical element set comprises:
   at least a lens of the first optical element set, wherein the light emitted from the light source passes through the lens of the first optical element set, the first diaphragm and the spectroscope in order, and then reaches the fundus.

6. The fundus optical image device according to claim 1, wherein the second optical element set further comprises:
   at least a second lens, wherein the second diaphragm is disposed between the first lens and the second lens.

7. The fundus optical image device according to claim 6, wherein the second lens is a curvature-adjustable lens.

8. The fundus optical image device according to claim 1, wherein the first diaphragm and the second diaphragm are both microarray diaphragms.

9. The fundus optical image device according to claim 1, further comprising:
   an observation module for observing the image of the fundus through the second optical element set.

10. The fundus optical image device according to claim 1, further comprising:
    an image capturing module for capturing the image of the fundus through the second optical element set.

* * * * *